US011213210B2

(12) United States Patent
Banerjee et al.

(10) Patent No.: US 11,213,210 B2
(45) Date of Patent: Jan. 4, 2022

(54) SYSTEM AND METHOD FOR CLASSIFICATION OF CORONARY ARTERY DISEASE BASED ON METADATA AND CARDIOVASCULAR SIGNALS

(71) Applicant: Tata Consultancy Services Limited, Mumbai (IN)

(72) Inventors: Rohan Banerjee, Kolkata (IN); Sakyajit Bhattacharya, Kolkata (IN); Soma Bandyopadhyay, Kolkata (IN); Arpan Pal, Kolkata (IN); Kayapanda Muthana Mandana, Kolkata (IN)

(73) Assignee: TATA CONSULTANCY SERVICES LIMITED, Mumbai (IN)

( * ) Notice: Subject to any disclaimer, the term of this patent is extended or adjusted under 35 U.S.C. 154(b) by 246 days.

(21) Appl. No.: 16/285,519

(22) Filed: Feb. 26, 2019

(65) Prior Publication Data
US 2019/0313920 A1  Oct. 17, 2019

(30) Foreign Application Priority Data

Mar. 16, 2018 (IN) .............................. 201821009796

(51) Int. Cl.
*A61B 5/02* (2006.01)
*G16H 50/30* (2018.01)
(Continued)

(52) U.S. Cl.
CPC ........ *A61B 5/02007* (2013.01); *A61B 5/7264* (2013.01); *A61B 5/7275* (2013.01);
(Continued)

(58) Field of Classification Search
None
See application file for complete search history.

(56) References Cited

U.S. PATENT DOCUMENTS

| 5,638,823 A | 6/1997 | Akay et al. | |
|---|---|---|---|
| 2005/0020903 A1* | 1/2005 | Krishnan | G16H 50/20 600/407 |
| 2013/0261484 A1* | 10/2013 | Schmidt | A61B 5/725 600/528 |

OTHER PUBLICATIONS

Forrester et al. ("Early Detection of Coronary Artery Disease" Adv Cardiol., vol. 26, pp. 1-14) (Year: 1979).*

(Continued)

*Primary Examiner* — Erica S Lee
(74) *Attorney, Agent, or Firm* — Finnegan, Henderson, Farabow, Garrett & Dunner LLP

(57) ABSTRACT

Non-invasive methods for accurately classifying Coronary Artery Disease (CAD) is a challenging task. In the present disclosure, a two stage classification is performed. In the first stage of classification, a metadata based rule engine is utilized to classify a subject into one of a confirmed CAD subject, a CAD subject and a non-CAD subject. Here, a set of optimal parameters are selected from a set of metadata associated with the subject based on a difference in frequency of occurrence of the CAD among a disease population and a non-disease population. Further, an optimal threshold associated with each optimal parameter is calculated based on an inflexion based correlation analysis. Further, the CAD subject, classified by the metadata based rule engine is further reclassified in a second stage by utilizing a set of cardiovascular signal into one of the CAD subject and the non-CAD subject.

7 Claims, 13 Drawing Sheets

(51) Int. Cl.
*A61B 5/00* (2006.01)
*G16H 50/20* (2018.01)
*A61B 5/024* (2006.01)
*A61B 7/04* (2006.01)

(52) U.S. Cl.
CPC .......... *G16H 50/30* (2018.01); *A61B 5/02416* (2013.01); *A61B 5/725* (2013.01); *A61B 5/7246* (2013.01); *A61B 5/7257* (2013.01); *A61B 7/04* (2013.01); *G16H 50/20* (2018.01)

(56) References Cited

OTHER PUBLICATIONS

Wang, J. et al. (Sep. 2014). "A correlation-based approach for determining the threshold value of singular value decomposition filtering for potential field data denoising," *Journal of Geophysics and Engineering*, vol. 11, No. 5; pp. 1-7.

Verma, L. et al. (2018). "An intelligent noninvasive model for coronary artery disease detection," *Complex Intelligent Systems*, vol. 4; pp. 11-18.

\* cited by examiner

SYSTEM AND METHOD FOR CLASSIFICATION OF CORONARY ARTERY DISEASE BASED ON METADATA AND CARDIOVASCULAR SIGNALS

PRIORITY CLAIM

This U.S. patent application claims priority under 35 U.S.C. § 119 to: India Application No. 201821009796, filed on Mar. 16, 2018. The entire contents of the aforementioned application are incorporated herein by reference.

TECHNICAL FIELD

The embodiments herein generally relates, in general, to health monitoring and, in particular, to a system and method for classification of Coronary Artery Disease (CAD) based on metadata and cardiovascular signals.

BACKGROUND

A Coronary Artery Disease (CAD), is a common cardiovascular disease affecting millions of people every year. The CAD typically occurs due to deposition of cholesterol and other fatty materials over time on the inner wall of a coronary artery. The deposition causes gradual loss of natural elastic property of the coronary artery and thereby restricting the free flow of blood in the coronary artery. The restriction of free flow of blood in the coronary artery causes chest pain (angina) and heart attack.

Typically, a Coronary Angiogram (CAG) is considered as a gold standard technique for clinically identifying the CAD along with the level of heart blockage. However, the CAG is an invasive procedure and is associated with mortality risk. Additionally, the CAG is not freely available and requires a modern hospital set-up to carry out. Moreover, the CAG may not detect an onset of CAD and there is a challenge in using the CAG as a mass screening system for detecting CAD. Moreover, the conventional methods for identifying the CAD are utilizing multiple cardiovascular biomedical signals including heart sound or phonocardiogram (PCG), electrocardiogram (ECG), photoplethysmogram (PPG) and the like. Moreover, demography, life style, self and family medical history of a subject also play important roles to estimate cardiac risk factor of the subject. Hence, there is a challenge in developing a method for an early non-invasive and accurate detection of the CAD.

SUMMARY

Embodiments of the present disclosure present technological improvements as solutions to one or more of the above-mentioned technical problems recognized by the inventors in conventional systems. For example, in one embodiment, a method for classification of Coronary Artery Disease (CAD) based on metadata and cardiovascular signals is provided. The method includes receiving, a set of metadata associated with a subject and a set of cardiovascular signal associated with the subject, wherein each metadata from the set of metadata is associated with a value, by the one or more hardware processors. Further, the method includes selecting, a set of optimal parameters from the set of metadata based on a difference in frequency of occurrence of CAD among a disease population and a non-disease population, by the one or more hardware processors. Furthermore, the method includes computing, an optimal threshold for each optimal parameter from the set of optimal parameters based on an inflexion point based correlation analysis, by the one or more hardware processors. Furthermore, the method includes classifying, the subject by utilizing a metadata based rule engine into a category among a plurality of categories, wherein the plurality of categories comprising a confirmed CAD subject, a CAD subject and a non-CAD subject, wherein the metadata based rule engine is constructed by utilizing the set of optimal parameters and the optimal threshold associated with each optimal parameter, by the one or more hardware processors. Furthermore, the method includes reclassifying, the CAD subject into one of the confirmed CAD subject and the non-CAD subject based on a combination of a PPG signal classifier and a PCG signal classifier in parallel, by the one or more hardware processors.

In another aspect, a system for classification of CAD based on metadata and cardiovascular signals is provided. The system includes one or more memories comprising programmed instructions and a repository for storing a set of metadata associated with a subject and a set of cardiovascular signal associated with the subject, one or more hardware processors operatively coupled to the one or more memories, wherein the one or more hardware processors are capable of executing the programmed instructions stored in the one or more memories, a PPG signal capturing unit, a PCG signal capturing unit and a CAD analysis unit, wherein the CAD analysis unit is configured to receive, a set of metadata associated with a subject and a set of cardiovascular signal associated with the subject, wherein each metadata from the set of meta data is associated with a value. Further, the CAD analysis unit is configured to select, a set of optimal parameters from the set of metadata based on a difference in frequency of occurrence of CAD among a disease population and a non-disease population. Furthermore the CAD analysis unit is configured to compute, an optimal threshold for each optimal parameter from the set of optimal parameters based on an inflexion point based correlation analysis. Furthermore, the CAD analysis unit is configured to classify, the subject by utilizing a metadata based rule engine into a category among a plurality of categories, wherein the plurality of categories comprising a confirmed CAD subject, a CAD subject and a non-CAD subject, wherein the metadata based rule engine is constructed by utilizing the set of optimal parameters and the optimal threshold associated with each optimal parameter. Furthermore, the CAD analysis unit is configured to reclassify, the CAD subject into one of the confirmed CAD subject and the non-CAD subject based on a combination of a PPG signal classifier and a PCG signal classifier in parallel.

In yet another aspect, a computer program product comprising a non-transitory computer-readable medium having embodied therein a computer program for system and method for classification of CAD based on metadata and cardiovascular signals, is provided. The computer readable program, when executed on a computing device, causes the computing device to receive, a set of metadata associated with a subject and a set of cardiovascular signal associated with the subject, wherein each metadata from the set of metadata is associated with a value. Further, the computer readable program, when executed on a computing device, causes the computing device to select, a set of optimal parameters from the set of metadata based on a difference in frequency of occurrence of CAD among a disease population and a non-disease population. Furthermore, the computer readable program, when executed on a computing device, causes the computing device to compute, an optimal threshold for each optimal parameter from the set of optimal parameters based on an inflexion point based correlation analysis. Furthermore, the computer readable program, when executed on a computing device, causes the computing device to classify, the subject by utilizing a metadata based rule engine into a category among a plurality of categories, wherein the plurality of categories comprising a confirmed CAD subject, a CAD subject and a non-CAD subject, wherein the metadata based rule engine is constructed by utilizing the set of optimal parameters and the optimal threshold associated with each optimal parameter. Furthermore, the computer readable program, when executed on a computing device, causes the computing device to reclassify, the CAD subject into one of the confirmed CAD subject and the non-CAD subject based on a combination of a PPG signal classifier and a PCG signal classifier in parallel.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

Figure 1:
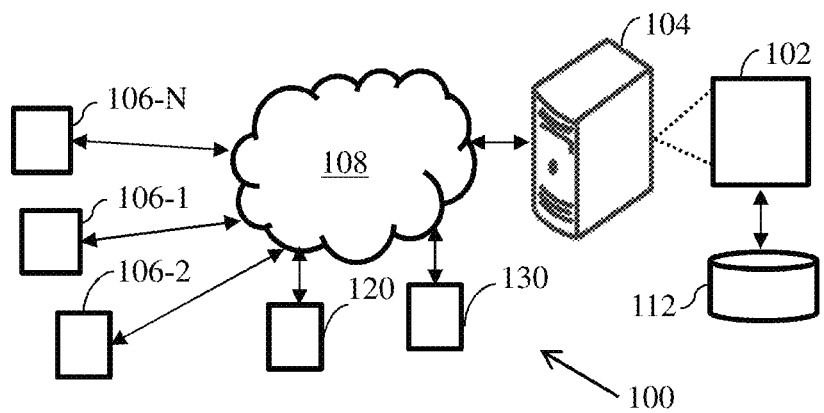
FIG. 1 illustrates a network environment implementing a system and method for classification of Coronary Artery Disease (CAD) based on metadata and cardiovascular signals, according to some embodiments of the present disclosure.

It should be appreciated by those skilled in the art that any block diagrams herein represent conceptual views of illustrative systems and devices embodying the principles of the present subject matter. Similarly, it will be appreciated that any flow charts, flow diagrams, and the like represent various processes which may be substantially represented in computer readable medium and so executed by a computer or processor, whether or not such computer or processor is explicitly shown.

DETAILED DESCRIPTION

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. It is intended that the following detailed description be considered as exemplary only, with the true scope and spirit being indicated by the following claims.

The present subject matter overcomes the limitations of the conventional Coronary Artery Detection (CAD) methods based on a non-invasive two stage classification approach. In the first stage of classification, a metadata based rule engine is utilized for classifying a subject as a confirmed CAD subject, a CAD subject and a non-CAD subject. Here, the metadata includes a set of demographic data associated with the subject, a set of clinical information associated with the subject and a medical history associated with the subject. The set of demographic data includes gender, age, weight and height. The set of clinical information includes Systolic Blood Pressure (SBP), Diastolic Blood Pressure (DBP), Body Mass Index (BMI) and lipid profile. The medical history includes smoking history, diabetes history, hypertension, chest pain, medication history of aspirin and statin, family history of diabetes, cardiac arrest and the like. The stage 1 classification can lead to a classification error associated with the CAD subject. The classification error associated with the CAD subject is further rectified by reclassifying the CAD subject by utilizing a second stage of classification based on a set of cardio vascular signals. In an embodiment, the set of cardiovascular signals includes a Photoplethysmogram (PPG) signal and a Phonocardiogram (PCG) signal. An implementation of the system and method for classification of Coronary Artery Disease (CAD) based on metadata and cardiovascular signals is described further in detail with reference to FIGS. 1 through 10.

Referring now to the drawings, and more particularly to FIGS. 1 through 10, where similar reference characters denote corresponding features consistently throughout the figures, there are shown preferred embodiments and these embodiments are described in the context of the following exemplary system and/or method.

FIG. 1 illustrates a network environment 100 implementing a system 102 for classification of CAD based on metadata and cardiovascular signals, according to some embodiments of the present disclosure. The system for classification of CAD based on metadata and cardiovascular signals 102, hereinafter referred to as the system 102, is configured for receiving the set of metadata associated with a subject and the set of cardiovascular signals associated with the subject. In an embodiment, the cardiovascular signals includes the PPG signal and the PCG signal. The PPG signal associated with the subject is recorded by utilizing the device 120. In an embodiment, the device 120 can be a commercially available pulse oximeter. The PCG signal associated with the subject is recorded by utilizing the device 130. In an embodiment, the device 130 can be a low-cost digital stethoscope. The system 102 may be embodied in a computing device, for instance a computing device 104.

Although the present disclosure is explained considering that the system 102 is implemented on a server, it may be understood that the system 102 may also be implemented in a variety of computing systems, such as a laptop computer, a desktop computer, a notebook, a workstation, a smartphone, a cloud-based computing environment and the like. In one implementation, the system 102 may be implemented in a cloud-based environment. It will be understood that the system 102 may be accessed by multiple users through one or more user devices 106-1, 106-2 . . . 106-N, collectively referred to as user devices 106 hereinafter, or applications residing on the user devices 106. Examples of the user devices 106 may include, but are not limited to, a portable computer, a personal digital assistant, a handheld device, a Smartphone, a Tablet Computer, a workstation and the like. The user devices 106 are communicatively coupled to the system 102 through a network 108.

In an embodiment, the network 108 may be a wireless or a wired network, or a combination thereof. In an example, the network 108 can be implemented as a computer network, as one of the different types of networks, such as virtual private network (VPN), intranet, local area network (LAN), wide area network (WAN), the internet, and such. The network 108 may either be a dedicated network or a shared network, which represents an association of the different types of networks that use a variety of protocols, for example, Hypertext Transfer Protocol (HTTP), Transmission Control Protocol/Internet Protocol (TCP/IP), and Wireless Application Protocol (WAP), to communicate with each other. Further, the network 108 may include a variety of network devices, including routers, bridges, servers, computing devices, storage devices. The network devices within the network 108 may interact with the system 102 through communication links.

As discussed above, the system 102 may be implemented in a computing device 104, such as a hand-held device, a laptop or other portable computer, a tablet computer, a mobile phone, a PDA, a smartphone, and a desktop computer. The system 102 may also be implemented in a workstation, a mainframe computer, a server, and a network server. In an embodiment, the system 102 may be coupled to a data repository, for example, a repository 112. The repository 112 may store data processed, received, and generated by the system 102. In an alternate embodiment, the system 102 may include the data repository 112. The components and functionalities of the system 102 are described further in detail with reference to FIG. 2.

Figure 2:
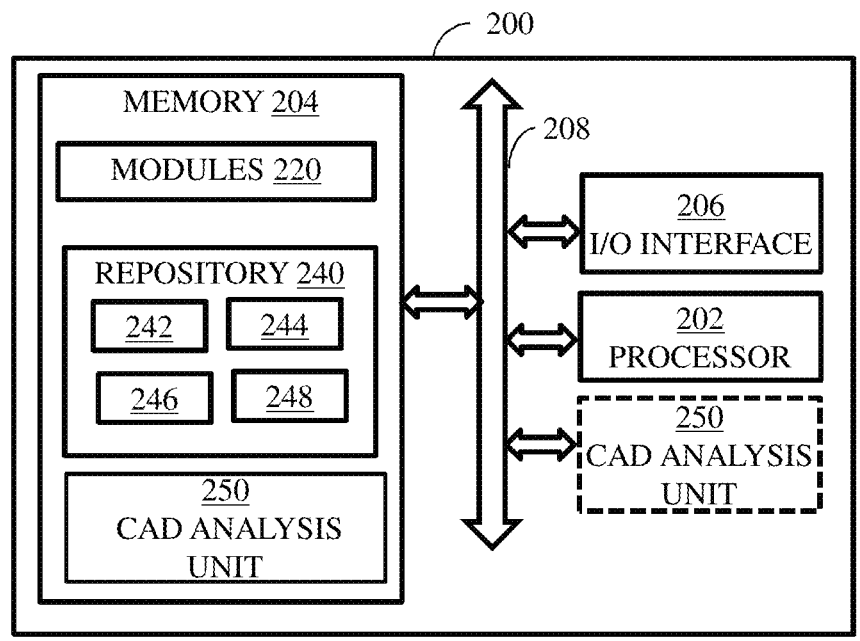
FIG. 2 illustrates a block diagram of the system for classification of CAD based on metadata and cardiovascular signals, according to some embodiments of the present disclosure.

FIG. 2 illustrates a block diagram of the system for classification of CAD based on metadata and cardiovascular signals, according to some embodiments of the present disclosure. The system for classification of CAD based on metadata and cardiovascular signals, 200 (hereinafter referred to as system 200) may be an example of the system 102 (FIG. 1). In an example embodiment, the system 200 may be embodied in, or is in direct communication with the system, for example the system 102 (FIG. 1). The system 200 includes or is otherwise in communication with one or more hardware processors such as a processor 202, at least one memory such as a memory 204, an I/O interface 206 and a CAD analysis unit 250. In an embodiment, the CAD analysis unit 250 can be implemented as a standalone unit in the system 200 comprising an optimal threshold computation module (not shown in FIG. 2), an optimal parameter selection module (not shown in FIG. 2), a metadata based classification module (not shown in FIG. 2) and a cardiovascular signal based reclassification module (not shown in FIG. 2). In another embodiment, the CAD analysis unit 250 can be implemented as a module in the memory 204 comprising the optimal threshold computation module (not shown in FIG. 2), the optimal parameter selection module (not shown in FIG. 2), the metadata based classification module (not shown in FIG. 2) and the cardiovascular signal based reclassification module (not shown in FIG. 2). The processor 202, memory 204, and the I/O interface 206 may be coupled by a system bus such as a system bus 208 or a similar mechanism.

The I/O interface 206 may include a variety of software and hardware interfaces, for example, a web interface, a graphical user interface, and the like. The interfaces 206 may include a variety of software and hardware interfaces, for example, interfaces for peripheral device(s), such as a keyboard, a mouse, an external memory, a camera device, and a printer. Further, the interfaces 206 may enable the system 102 to communicate with other devices, such as web servers and external databases. The interfaces 206 can facilitate multiple communications within a wide variety of networks and protocol types, including wired networks, for example, local area network (LAN), cable, etc., and wireless networks, such as Wireless LAN (WLAN), cellular, or satellite. For the purpose, the interfaces 206 may include one or more ports for connecting a number of computing systems with one another or to another server computer. The I/O interface 206 may include one or more ports for connecting a number of devices to one another or to another server.

The hardware processor 202 may be implemented as one or more microprocessors, microcomputers, microcontrollers, digital signal processors, central processing units, state machines, logic circuitries, and/or any devices that manipulate signals based on operational instructions. Among other capabilities, the hardware processor 202 is configured to fetch and execute computer-readable instructions stored in the memory 204.

The memory 204 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. In an embodiment, the memory 204 includes a plurality of modules 220 and a repository 240 for storing data processed, received, and generated by one or more of the modules 220 and the CAD analysis unit 250. The modules 220 may include routines, programs, objects, components, data structures, and so on, which perform particular tasks or implement particular abstract data types.

The memory 204 also includes module(s) 220 and a data repository 240. The module(s) 220 include programs or coded instructions that supplement applications or functions performed by the system 200 for classification of CAD based on metadata and cardiovascular signals. The modules 220, amongst other things, can include routines, programs, objects, components, and data structures, which perform particular tasks or implement particular abstract data types. The modules 220 may also be used as, signal processor(s), state machine(s), logic circuitries, and/or any other device or component that manipulates signals based on operational instructions. Further, the modules 220 can be used by hardware, by computer-readable instructions executed by a processing unit, or by a combination thereof. The modules 220 can include various sub-modules (not shown). The modules 220 may include computer-readable instructions that supplement applications or functions performed by the system 200 for classification of CAD based on metadata and cardiovascular signals.

The data repository 240 may include received set of metadata 242, the PPG signal data 244, the PCG signal data 246 and other data 248. Further, the other data 248 amongst other things, may serve as a repository for storing data that is processed, received, or generated as a result of the execution of one or more modules in the module(s) 220 and the modules associated with the CAD analysis unit 250. The repository 240 is further configured to maintain a plurality of parameters associated with the set of metadata, the PPG signal data and the PCG signal data stored in the data repository 240.

Although the data repository 240 is shown internal to the system 200 for classification of CAD based on metadata and cardiovascular signals, it will be noted that, in alternate embodiments, the data repository 240 can also be implemented external to the system 200 for classification of CAD based on metadata and cardiovascular signals, where the data repository 240 may be stored within a database (not shown in FIG. 2) communicatively coupled to the system 200 for classification of CAD based on metadata and cardiovascular signals. The data contained within such external database may be periodically updated. For example, new data may be added into the database (not shown in FIG. 2) and/or existing data may be modified and/or non-useful data may be deleted from the database (not shown in FIG. 2). In one example, the data may be stored in an external system, such as a Lightweight Directory Access Protocol (LDAP) directory and a Relational Database Management System (RDBMS). In another embodiment, the data stored in the data repository 240 may be distributed between the system 200 for classification of CAD based on metadata and cardiovascular signals and the external database.

Figure 3:
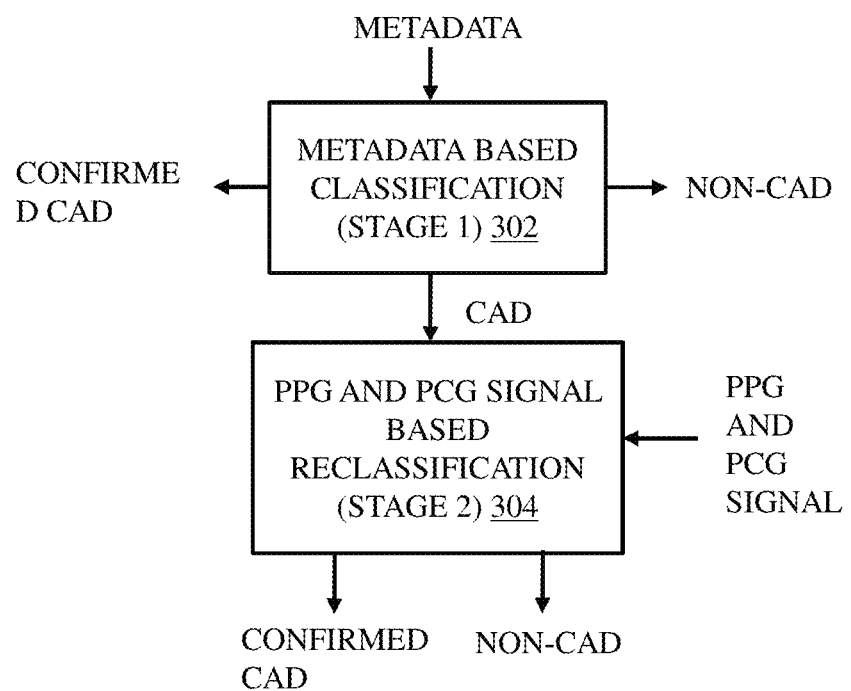
FIG. 3 depicts an example architecture for CAD classification, according to some embodiments of the present disclosure.

FIG. 3 depicts an example architecture for CAD classification, according to some embodiments of the present disclosure. Now referring to FIG. 3, the set of metadata associated with the subject are received by the metadata based classification module (stage 1) 302. Here, a set of optimal parameters are chosen from the set of metadata, based on a difference in frequency of occurrence of CAD among a disease population and a non-disease population. Further, an optimal threshold associated with each parameter from the set of optimal parameters is obtained by utilizing an inflexion point based correlation analysis. Further, a set of rules are created by utilizing the set of optimal parameters and the optimal threshold associated with each optimal parameter. Further, the metadata based rule engine is constructed by utilizing the set of rules and the subject is classified into one of the confirmed CAD subject, the CAD subject and the non-CAD subject. Here, the CAD subject undergoes a reclassification (stage 2) 304 and the reclassification is based on the PPG signal parameters and the PCG signal parameters. Here, a set of PPG signal parameters are extracted from the PPG signal and a set of PCG signal parameters are extracted from the PCG signal in parallel. Further, the set of PPG signal parameters are classified by utilizing a pre-trained PPG signal classifier to obtain a first confidence score and the set of PCG signal parameters are classified by utilizing a pre-trained PCG signal classifier to obtain a second confidence score. Further, the first confidence score and the second confidence score are compared and a decision associated with the highest score among the first confidence score and the second confidence score is utilized to classify the CAD subject into one of the confirmed CAD subject and the non-CAD subject. In an embodiment, the reclassification of the subject as one of the confirmed CAD subject and the non-CAD subject is displayed on the smart phone.

The CAD analysis unit 250 of the CAD classification system 200 can be configured to receive the set of metadata associated with the subject and the set of cardiovascular signals associated with the subject, wherein each metadata from the set of metadata is associated with a value. Here, the metadata includes the set of demographic data associated with the subject, the set of clinical information associated with the subject and the medical history associated with the subject. The set of demographic data includes gender, age, weight and height. The set of clinical information includes Systolic Blood Pressure (SBP), Diastolic Blood Pressure (DBP), Body Mass Index (BMI) and lipid profile. Here, $MAP = \frac{1}{3} \times SBP + \frac{2}{3} \times DBP$. The medical history includes smoking history, diabetes history, hypertension, chest pain, medication history of aspirin and statin, family history of diabetes, cardiac arrest and the like. In an embodiment, the cardiovascular signals includes the PPG signal and the PCG signal. In an embodiment, the PPG signal associated with the CAD subject is recorded from the right hand index finger by utilizing a commercially available non-medical grade fingertip CONTEC™ Medical Systems (CMS) 50D+ pulse-oximeter at a sampling rate of 60 Hz. The CMS 50D+ pulse-oximeter is connected to the smart phone via a Universal Serial Bus-On-The-Go (USB-OTG) cable or via Bluetooth and is capable of storing the recorded PPG signal via USB interface for offline processing. Further, a signal quality assessment algorithm based on PPG morphology is applied to extract 2 minutes of good quality PPG signal from the subject for further processing. The duration of recording ensures to preserve the Heart Rate Variability (HRV) related information in the collected signal and also a low computation time for sending the recorded data to server, feature extraction and classification. In parallel, the PCG signal associated with the CAD subject is recorded by utilizing a low cost in-house digital stethoscope. The low cost in-house digital stethoscope is capable of storing multiple PCG signal recordings simultaneously and is connected to the smart phone via 3.5 mm audio jack. Here, the PCG signal is recorded for 30 seconds and the quality of the PCG signal is assessed by utilizing a PCG signal quality assessment module associated with the smart phone. Here, the audio sampling rate of the PCG signal is predefined at 8000 Hz and the PCG signals are recorded from left third intercostal space of the subject. The subject is in supine position during the recording of the PCG signal.

Figure 4A:
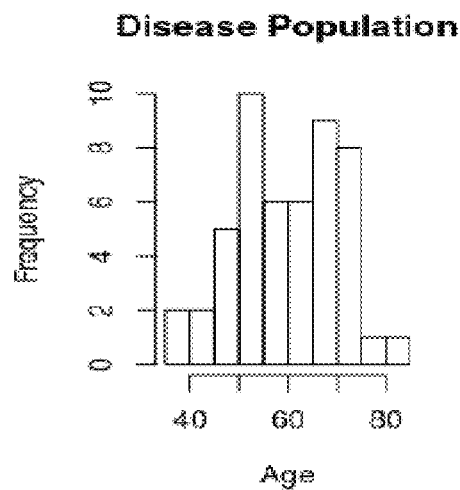
FIG. 4A depicts an example histogram associated with a disease population for age parameter, according to some embodiments of the present disclosure.
Figure 4B:
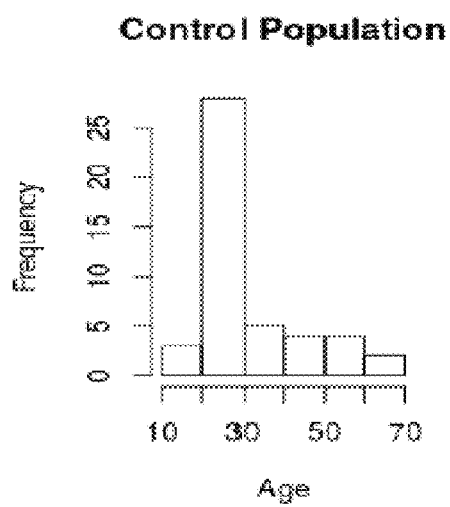
FIG. 4B depicts an example histogram associated with a non-disease population for age parameter, according to some embodiments of the present disclosure.

Further, CAD analysis unit 250 of the CAD classification system can be configured to select a set of optimal parameters from the set of metadata based on a difference in frequency of occurrence of CAD among the disease population and the non-disease population. In an embodiment, seven metadata are selected as optimal parameters. The seven optimal parameters includes age, diabetes, Maximum Arterial Pressure (MAP), hypertension, family cardiac history, BMI and chest pain. From medical domain, it is evident that if a subject belongs to a relatively high age group and is of diabetic then he/she has high probability of getting CAD. In an embodiment, the method of selecting the set of optimal parameters from the set of metadata based on a difference in frequency of occurrence of CAD among the disease population and the non-disease population is explained with reference to FIG. 4A to 4D. FIG. 4A depicts an example histogram associated with the disease population for age parameter, according to some embodiments of the present disclosure. Now referring to FIG. 4A, age of the subject under the disease population is plotted along an X plane and a frequency of occurrence of the CAD among the disease population is plotted along a Y plane. Here, the frequency of occurrence of the CAD disease under the disease population increases as the age associated with the disease population increases. FIG. 4B depicts an example histogram associated with the control population for age parameter, according to some embodiments of the present disclosure. Now referring to FIG. 4B, age of the subject under the non-disease population is plotted along an X plane and a frequency of occurrence of the CAD among the non-disease population is plotted along a Y plane. Here, the frequency of occurrence of the CAD disease under the non-disease population has less impact on the age associated with the non-disease population increases. Hence, the heuristic, "age has a significant relation with the CAD" is verified based on FIG. 4A and FIG. 4B. The said heuristic can be supported medically, as older people start losing natural elastic properties of arteries, causing narrowing of coronary artery.

Figure 4C:
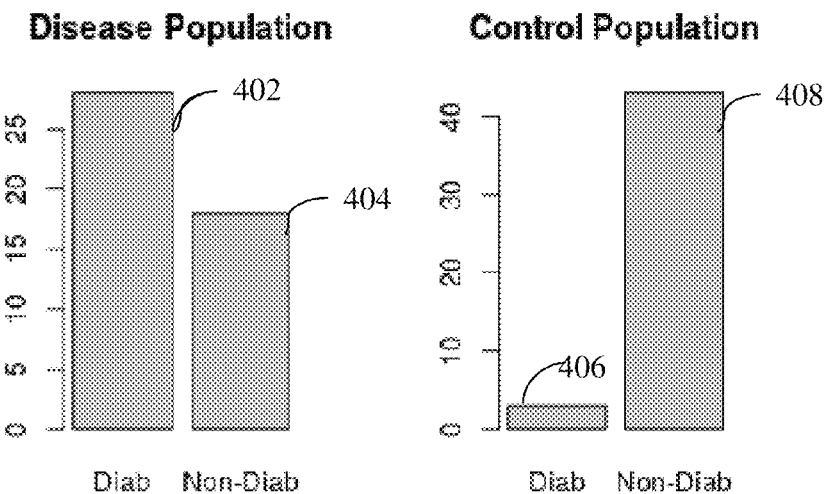
FIG. 4C depicts an example bar diagram, comparing a number of diabetic subjects and a number of non-diabetic subjects in the disease population and in the non-disease population, according to some embodiments of the present disclosure.

FIG. 4C depicts an example bar diagram, comparing a number of diabetic subjects and a number of non-diabetic subjects in the disease population and in the non-disease population, according to some embodiments of the present disclosure. Now, referring to FIG. 4C, the Y plane indicates the age associated with the disease population and the non-disease population. Here, a histogram 402 indicates the number of diabetic subjects in the disease population, a histogram 404 indicates the number of non-diabetic subjects in the disease population, a histogram 406 indicates the number of diabetic subjects in the non-disease population and a histogram 408 indicates the number of non-diabetic subjects in the non-disease population. Here, while comparing the number of diabetic subjects 402 in the disease population and the number of diabetic subjects 406 in the non-disease population, the number of diabetic subjects are more in the disease population than the number of diabetic subjects in the non-disease population. Hence, the subject above 40 years of age and with diabetics are having high probability to have CAD.

Figure 4D:
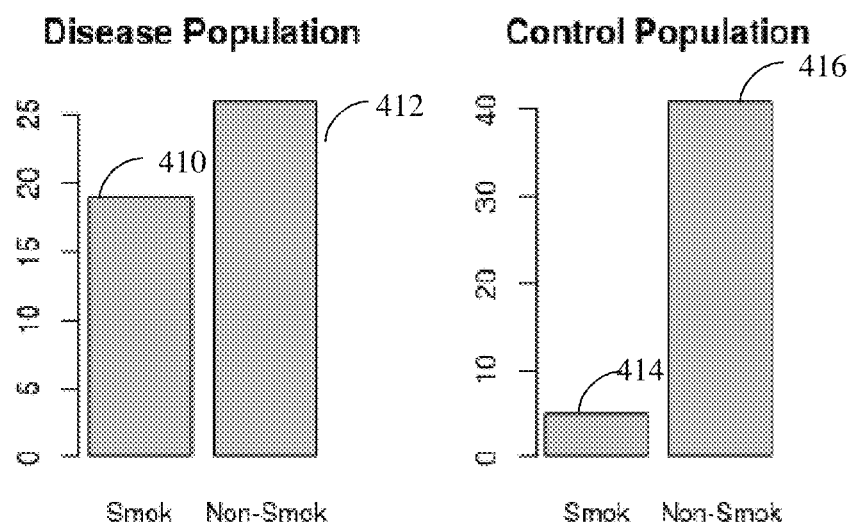
FIG. 4D depicts an example bar diagram comparing a number of smoking subjects and a number of non-smoking subjects in the disease population and in the non-disease population, according to some embodiments of the present disclosure.

FIG. 4D depicts an example bar diagram comparing a number of smoking subjects and a number of non-smoking subjects in the disease population and in the non-disease population, according to some embodiments of the present disclosure. Now, referring to FIG. 4D, the Y plane indicates the age associated with the disease population and the non-disease population. Here, a histogram 410 indicates the number of smoking subjects in the disease population, a histogram 412 indicates the number of non-smoking subjects in the disease population, a histogram 414 indicates the number of smoking subjects in the non-disease population and a histogram 416 indicates the number of non-smoking subjects in the non-disease population. Here, while comparing the number of smoking subjects 410 in the disease population and the number of smoking subjects 414 in the non-disease population, the number of smoking subjects are more in the disease population than the number of smoking subjects in the non-disease population. Hence, the subject above 40 years of age and with smoking habit are having high probability to have CAD. Similarly, the set of optimal parameters are selected from the set of metadata based on the difference in frequency of occurrence of CAD among the disease population and the non-disease population.

Figure 4E:
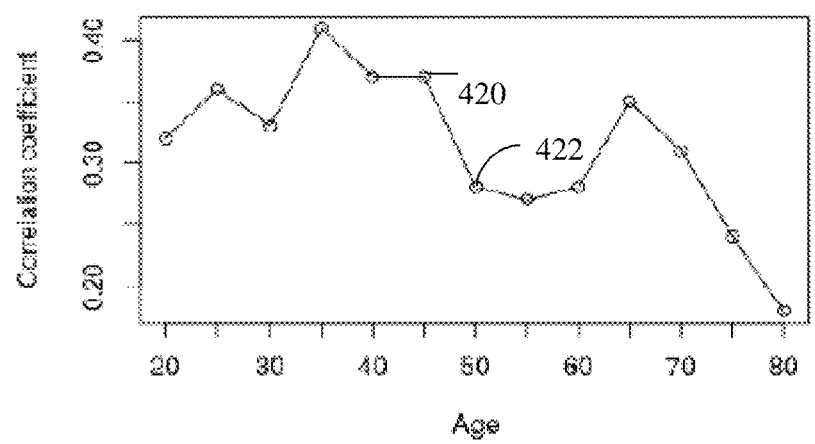
FIG. 4E depicts an example two dimensional plot illustrating a set of correlation coefficients between the disease population and the non-disease population corresponding to the age parameter, according to some embodiments of the present disclosure.

Further, CAD analysis unit 250 of the CAD classification system can be further configured to identify an optimal threshold for each metadata from the set of metadata based on the inflexion point based correlation analysis. Here, the inflexion point based correlation analysis is performed as follows: (i) Select an age point T and remove all subjects of age less than or equal to T to obtain a set of subjects. (ii) calculate a correlation coefficient (r) between a histogram associated with the disease population and a histogram associated with the non-disease population by utilizing Bhattacharya distance. (iii) construct an XY plot, wherein the optimal parameter associated with the subject is plotted along an X plane and the correlation coefficient is plotted along a Y plane. (iv) compare each point in the XY plot with the previous point to identify any decrease or increase in correlation coefficient (r) from the previous point. If a highest inflexion occurs between the present point and the previous point, select the previous point as the optimum threshold value. FIG. 4E depicts an example two dimensional plot illustrating a set of correlation coefficients between the disease population and the non-disease population corresponding to the age parameter, according to some embodiments of the present disclosure. Now, referring to FIG. 4E, age of the subject is plotted along an X plane and the correlation coefficient is plotted along a Y plane. Here, the highest inflexion occurs between the point 420 (age=45) and the point 422. Since the highest inflexion occurred at age 45, age=45 is selected as the optimal threshold. In the same way, the optimal threshold associated with each optimal parameter from the set of optimal parameters are calculated by utilizing the inflexion point based correlation analysis.

Figure 5:
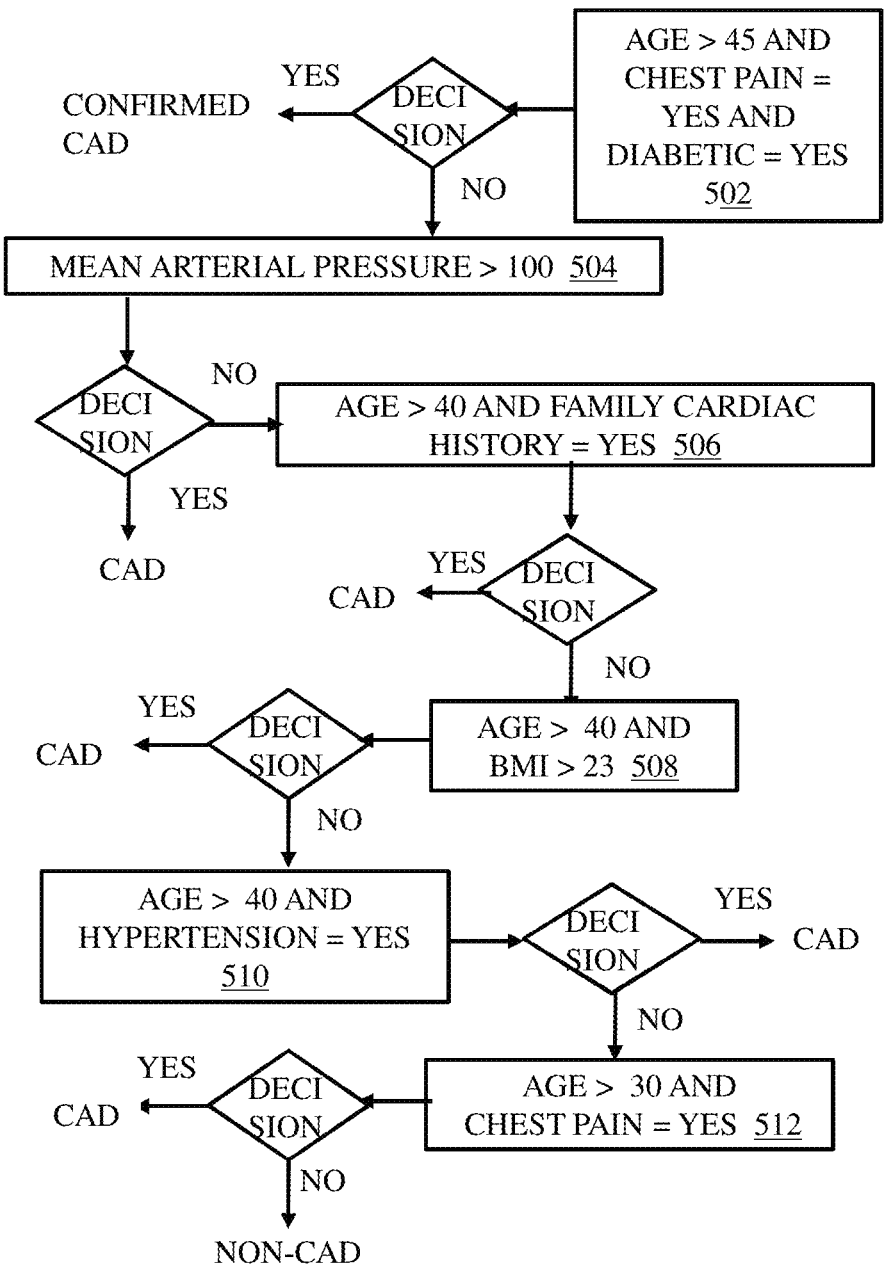
FIG. 5 depicts an example metadata based rule engine, according to some embodiments of the present disclosure.

Further the CAD analysis unit 250 of the CAD classification system can be configured to classify the subject by utilizing the metadata based rule engine into a category among a plurality of categories, wherein the plurality of categories comprising the confirmed CAD subject, the CAD subject and the non-CAD subject, wherein the metadata based rule engine is constructed by utilizing the set of optimal parameters and the optimal threshold associated with each optimal parameter. FIG. 5 depicts an example metadata based rule engine, according to some embodiments of the present disclosure. Now, referring to FIG. 5, at step 502, the subject is tested for age, diabetic and chest pain. If the age is more than 45 years, if the subject is diabetic, and if the subject is with chest pain, the subject is classified as the confirmed CAD subject by the metadata based rule engine. If the above condition at step 502 is not satisfied, the MAP of the subject is tested at step 504 and if the MAP is greater than 100, the subject is classified as the CAD subject. If the MAP is less than or equal to 100, the subject is tested for age and cardiac activity at step 506. If the age is greater than 40 years and if the subject is having family cardiac history, then the subject is classified as the CAD subject. Otherwise, age and BMI associated with the subject is tested at step 508. If the age is greater than 40 and BMI is greater than 23, then the subject is classified as the CAD subject. Otherwise, the subject is tested for age and hypertension at step 510. If the age of the subject is greater than 40 and the subject is having hypertension, then the subject is classified as the CAD subject. Otherwise, the subject is tested for age and chest pain at step 512. If the age of the subject is greater than 30 and the subject is having chest pain, then the subject is classified as the CAD subject. Otherwise, the subject is classified as the non-CAD subject. In an embodiment, the metadata based rule engine is trained with a 5-fold cross validation data. Additionally, the 5-fold cross validation data is utilized for tuning the hyper parameters associated with the metadata based rule engine.

Figure 6A:
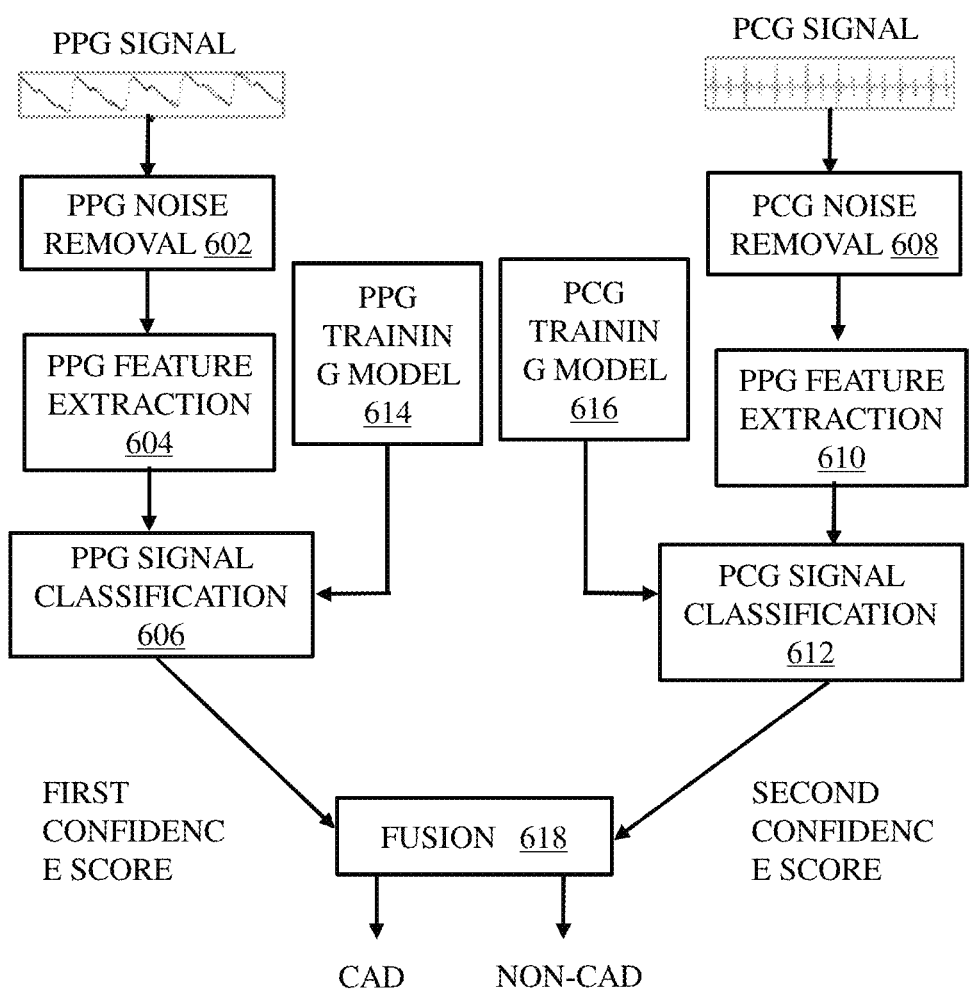
FIG. 6A depicts an example architecture for cardiovascular signal based reclassification, according to some embodiments of the present disclosure.

Further, the CAD analysis unit 250 of the CAD classification system can be configured to reclassify, the CAD subject into one of the confirmed CAD subject and the non-CAD subject based on a combination of the PPG signal classifier and the PCG signal classifier in parallel. FIG. 6A depicts an example architecture for cardiovascular signal based reclassification, according to some embodiments of the present disclosure. Now, referring to FIG. 6A, the PPG signal and the PCG signal associated with the CAD subject is received and processed as follows: the PPG signal measures a volumetric blood flow in capillaries and a fundamental frequency of the PPG signal indicates a heart rate associated with the subject. The PPG signal captured by utilizing the pulse-oximeter may be associated with a noise. At step 602, the noise associated with the PPG signal is removed. Here, the PPG signal associated with the noise is fed into a Butterworth low pass filter with a cut-off frequencies of 0.5 Hz and 10 Hz to remove a plurality of undesired frequency components. Further, a set of PPG signal parameters are extracted at step 604. In parallel, a noise associated with the PCG signal is removed at step 608 and a set of PCG signal parameters are extracted from the PCG signal at step 610. At step 606, the set of PPG signal parameters are classified by utilizing a pre-trained PPG signal classifier to obtain a first confidence score. At step 612, the set of PCG signal parameters are classified by utilizing a pre-trained PCG signal classifier to obtain a second confidence score in parallel. In an embodiment, a nonlinear Support Vector Machine (SVM) with Radial Basis Function (RBF) kernel is used as the PPG and the PCG signal classifier. Here, the PPG signal classifier is pre-trained by utilizing a PPG training model 614 and the PCG signal classifier is pre-trained by utilizing a PCG training model 616. The SVM separates two classes in a multidimensional feature space by fitting an optimal separating hyperplane (OSH) to the training samples. The objective function of SVM aims to maximize the margin between the hyperplane and the closest training samples, known as support vectors. Thus, for a given test data point, if the distance to the hyperplane is higher, then the output class label is more reliable. Further, the first confidence score from the PPG signal classifier and the second confidence score from the PCG signal classifier are fused at step 618 to obtain a final classification of the CAD subject into one among the CAD subject and the non-CAD subject. Here, a maximum confidence score is obtained by comparing the first confidence score and the second confidence score and the final classification of the subject is based on the maximum confidence score. For example, if the first confidence score is 0.78 for the confirmed CAD subject and 0.22 for the non-CAD subject. The second confidence score is 0.45 for the confirmed CAD subject and 0.65 for the non-CAD subject, the subject is decided as the confirmed CAD subject based on the first confidence score for the confirmed CAD subject.

Figure 6B:
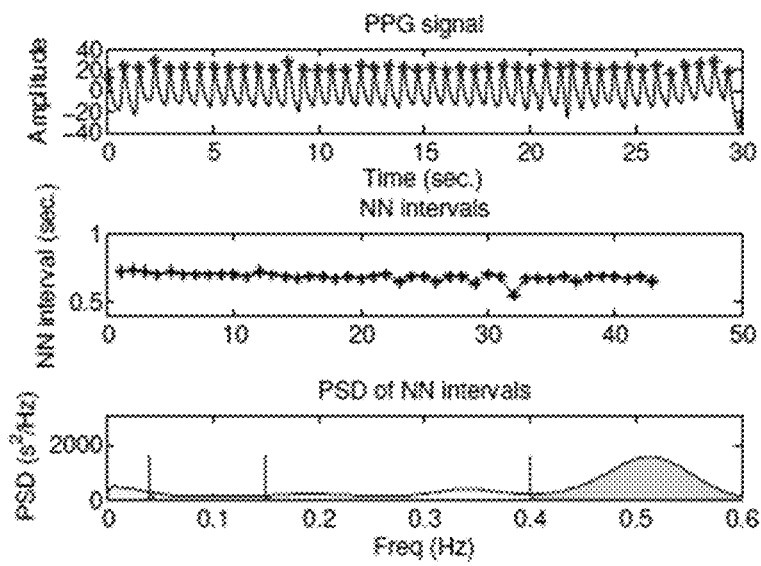
FIG. 6B depicts an example Power Spectral Density (PSD) plot of Heart Rate Variability (HRV) signals, for a sample CAD subject, according to some embodiments of the present disclosure.
Figure 6C:
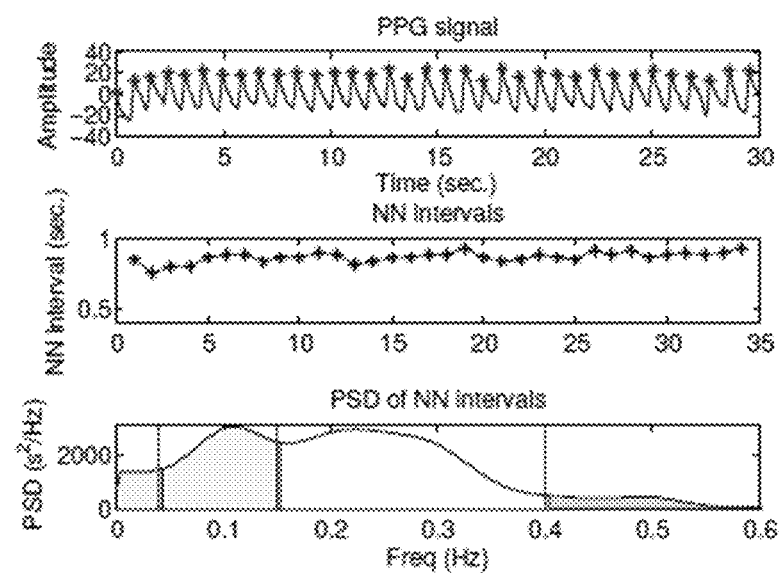
FIG. 6C depicts an example Power Spectral Density (PSD) plot of HRV signals, for a non-CAD subject, according to some embodiments of the present disclosure.
Figure 6D:
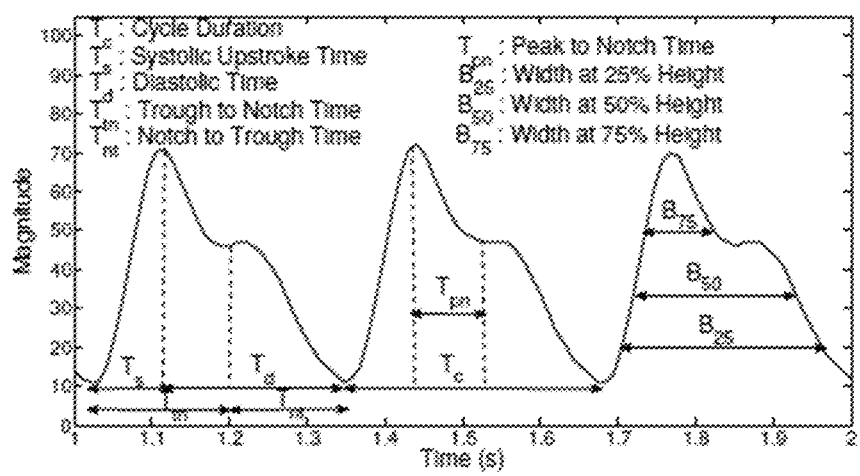
FIG. 6D depicts an example PPG signal with the set of PPG signal parameters, according to some embodiments of the present disclosure.

In an embodiment, the set of PPG signal parameters includes a plurality of morphological PPG features, a plurality of time domain PPG features and a plurality of frequency domain PPG features associated with the PPG signal. Here, the plurality of morphological PPG features includes a rising time, a falling time, a rising to falling tile ration and pulse width. In an embodiment, a plurality of morphological features and frequency domain features are extracted from a spectrum of HRV signal as follows: Here, the CAD subjects includes a lesser HRV signal compared to non-CAD subjects. Here, a peak to peak interval distance time series obtained from the PPG signal is termed as HRV signal. For brevity of description, the peak to peak interval distance time series is alternatively represented as NN interval (interval between normal peaks). Initially, an unequal sampling rate of the HRV signal is set to a fixed sampling rate of 2 Hz using cubic spline technique. Further, spectral analysis is performed on the HRV signal based on Welch's algorithm, to estimate the power spectrum of the HRV signal using an averaging modified periodogram. Here, the power spectrum of the HRV signal is divided into 3 bands, namely, very low frequency (V LF, 0-0.04 Hz), low frequency (LF, 0.04-0.15 Hz) and high frequency (HF, 0.15-0.4 Hz) regions. The normalized spectral power within the 3 frequency bands (nVLF, nLF, nHF) with respect to total spectral power are computed as features. The LF region is typically considered as markers of sympathetic modulation and the HF region contains the rhythms regulated by parasympathetic activities. FIG. 6B depicts an example Power Spectral Density (PSD) plot of HRV signals, for a sample CAD subject, according to some embodiments of the present disclosure. FIG. 6C depicts an example Power Spectral Density (PSD) plot of HRV signals, for a sample non-CAD subject, according to some embodiments of the present disclosure. Now, referring to FIG. 6B and FIG. 6C, the duration of measurement is fixed for half a minute. It can be observed that the spectral power contents for all the 3 frequency regions (V LF, LF and HF) is much lesser for a CAD patient, due to the reduced HRV compared to a non-CAD subject. In an embodiment, the plurality of time domain features associated with the PPG signal are extracted as follows: FIG. 6D depicts an example PPG signal with the set of PPG signal parameters, according to some embodiments of the present disclosure. Now referring to FIG. 6D, a sample PPG signal indicating some of the commonly used features are shown. Each cycle of a PPG waveform includes two terminal trough points and a peak corresponding to diastole and systole. A diccrotic notch is located in between the peak and succeeding trough. The plurality of time domain PPG features includes (1) mean of pulse width ($T_c$) (2) standard deviation of pulse width ($T_c$) (3) mean of relative crest time ($T_1=T_s/T_c$), 4) standard deviation of relative crest time ($T_2=T_d/T_c$) (6) standard deviation of relative diastolic time (7) mean of time ratio between crest time and diastolic time ($R=T_s/T_d$) and (8) standard deviation of R, calculated from every recording. Here, $T_s$ is the Crest time, $T_d$ is the Diastolic Time, $T_c$ is the Pulse Width, pk2pk is the Peak to peak interval, $B_{33}$ is the Pulse width at 33% height and $B_{75}$ is the Pulse width at 75% height. Table 1 illustrates the set of PPG signal parameters and a range of values associated with the CAD subject and the non-CAD subject. Further, the set of PPG signal parameters are classified by utilizing a pre-trained PPG signal classifier to obtain a first confidence score. Here, the PPG signal classifier is pre-trained by utilizing a PPG training model 614.

In an embodiment, the set of PCG signal parameters includes a plurality of PCG morphological features, a plurality of time domain PCG features and a plurality of frequency domain PCG features. Here, the plurality of PCG morphological features includes, a Systole_1 to Systole_2 duration, a spectral power, a systolic width, a diastolic width etc. Here, fundamental heart sounds including a systolic region and a diastolic region associated with each cardiac cycle are identified from the PCG signal in a typical segmentation based approach. Here, a set of time domain PCG features and a set of frequency domain PCG features are extracted from the segmented regions of the PCG signal. The segmentation based approach requires an automatic segregation of the fundamental heart sounds. Further a non-segmentation based approach is utilized for heart sound analysis. Further, a low pass filter is used to remove all the frequency components above 500 Hz. The selection of the cut-off frequency of the filter ensures to preserve the relevant information regarding cardiac functionalities and removes all high frequency noise components. In order to compute features corresponding to individual heartbeat, the entire recording is processed by splitting into small windows, using rectangular window having 50% overlapping. Since heart rate of a stable cardiac subject does not go below 30 BPM (Beats Per Minute), a window length of 2 seconds duration ensures the presence of at least one complete heart beat in every window. The final feature set for creating the classifier is selected based on Maximal Information Coefficient (MIC). Further, a Short Time Fourier Transform (STFT) corresponding to every window of the PCG recording is computed to get the spectrum, for extracting the set of frequency domain PCG features. For kth time window $W_k(t)$, the amplitude of spectral power in frequency domain is denoted by $S_k(\omega)$ and N is the length of the window for expressing the set of frequency domain PCG features. Here, the set of PCG signal parameters includes a Ratio of spectral power, a spectral centroid, a spectral roll-off, a spectral flux, a kurtosis of the time signal in a window, a natural entropy and Tsallis entropy. Table 2 illustrates the set of PCG signal parameters and a range of values associated with the CAD subject and the non-CAD subject.

Ratio of spectral power between 0-100 Hz and 100-150 Hz: ($R=P_{0-100}/P_{100-150}$). The frequency components present in the heart sound spectrum of the CAD patient above 100 Hz are significant and hence the numerical value of the parameter R is typically found more for a non-CAD subject compared to the CAD subject.

Spectral centroid: The spectral centroid as given in equation 1 indicates the frequency region, where most of the spectral energy is converged. Since the number of frequency components are more above 100 Hz for the CAD subject, the frequency centroid is shifted more towards the right-side of the spectrum.

$$cen = \Sigma_{\omega=1}^{N} \omega * S_k(\omega) / \Sigma_{\omega=1}^{N} \omega \quad (1)$$

Spectral roll-off: The spectral roll-off as given in equation 2 measures the region, containing 85% of the total spectral energy.

$$SR = 0.85 * \Sigma_{\omega=1}^{N} S_k(\omega) \quad (2)$$

Spectral flux: The spectral flux as given on equation 3 measures absolute difference in spectral energy between two successive windows. A higher value of the spectral flux parameter indicates a rapid fluctuation in heart sounds in successive heart beats.

$$SF = (\|S_k(\omega) - S_{k-1}(\omega)\|) \quad (3)$$

The Natural entropy H (x) and the Tsallis entropy $S_q(x)$ are as given in equation 4 and equation 5.

$$H(x) = -\sum_i prob(x_i) \ln(p(x_i)) \quad (4)$$

$$S_q(x) = \frac{k}{q-1}\left(1 - \sum_i prob(x_i^q)\right) \quad (5)$$

Where, $prob(x_i)$ is the probability of ith PCG sample, $x_i$, k and q are real parameters equal to 1 and 2 respectively. Table 2 shows the range of different PCG features for CAD and non-CAD subjects obtained from our dataset. It is to be noted that, the reported values of the frequency features are calculated in terms of FFT points not in Hz. It can be observed that CAD patients typically exhibit higher values of spectral centroid, spectral roll off but lower spectral power ratio. PCG signals of CAD subjects often show more irregularities than non-CAD subjects, resulting in higher numerical values of spectral flux, natural and Tsallis entropy.

TABLE 1

Ranges of PPG features for the CAD and the non-CAD subjects.

| Sl. No | PPG features | CAD range Mean ± SD | Non-CAD range Mean ± SD |
|---|---|---|---|
| 1. | Spectral power of NN intervals in 0-0.04 Hz | 0.99 ± 0.3 | 1.31 ± 0.3 |
| 2. | Spectral power of NN intervals in 0.04-0.15 Hz | 0.05 ± 0.02 | 0.08 ± 0.01 |
| 3. | Spectral power of NN intervals in 0.15-0.4 Hz | 0.006 ± 0.001 | 0.008 ± 0.001 |
| 4. | Mean of pulse duration ($T_c$) in seconds | 0.75 ± 0.14 | 0.84 ± 0.15 |
| 5. | Standard Deviation (SD) of pulse duration ($T_c$) | 0.07 ± 0.05 | 0.09 ± 0.05 |
| 6. | Mean of relative crest time ($T_s/T_c$) | 0.29 ± 0.04 | 0.27 ± 0.03 |
| 7. | SD of relative crest time ($T_s/T_c$) | 0.02 ± 0.01 | 0.03 ± 0.01 |
| 8. | Mean of relative diastolic time ($T_d/T_c$) | 0.71 ± 0.04 | 0.73 ± 0.03 |
| 9. | SD of relative diastolic time ($T_d/T_c$) | 0.03 ± 0.01 | 0.04 ± 0.02 |
| 10. | Mean of time ratio ($T_d/T_s$) | 2.49 ± 0.49 | 2.81 ± 0.53 |
| 11. | SD of time ratio time ($T_d/T_s$) | 0.35 ± 0.25 | 0.43 ± 0.19 |

TABLE 2

Ranges of PCG features for CAD and non-CAD subjects.

| Sl. No | PCG features | CAD range Mean ± SD | Non-CAD range Mean ± SD |
|---|---|---|---|
| 1. | Spectral power ratio between 0-100 Hz and 100-150 Hz | 0.031 ± 0.017 | 0.041 ± 0.012 |
| 2. | Spectral centroid | 602 ± 83 | 579 ± 92 |
| 3. | Spectral roll-off | 2902 ± 1754 | 2745 ± 1681 |
| 4. | Spectral flux | 118.44 ± 51.23 | 96.77 ± 48.73 |
| 5. | Kurtosis of time windows | 21.23 ± 5.1 | 27.62 ± 8.3 |
| 6. | Natural entropy | 123.33 ± 40.1 | 92.5 ± 38.96 |
| 7. | Tsallis entropy | 1053 ± 434 | 887 ± 376 |

Figure 7:
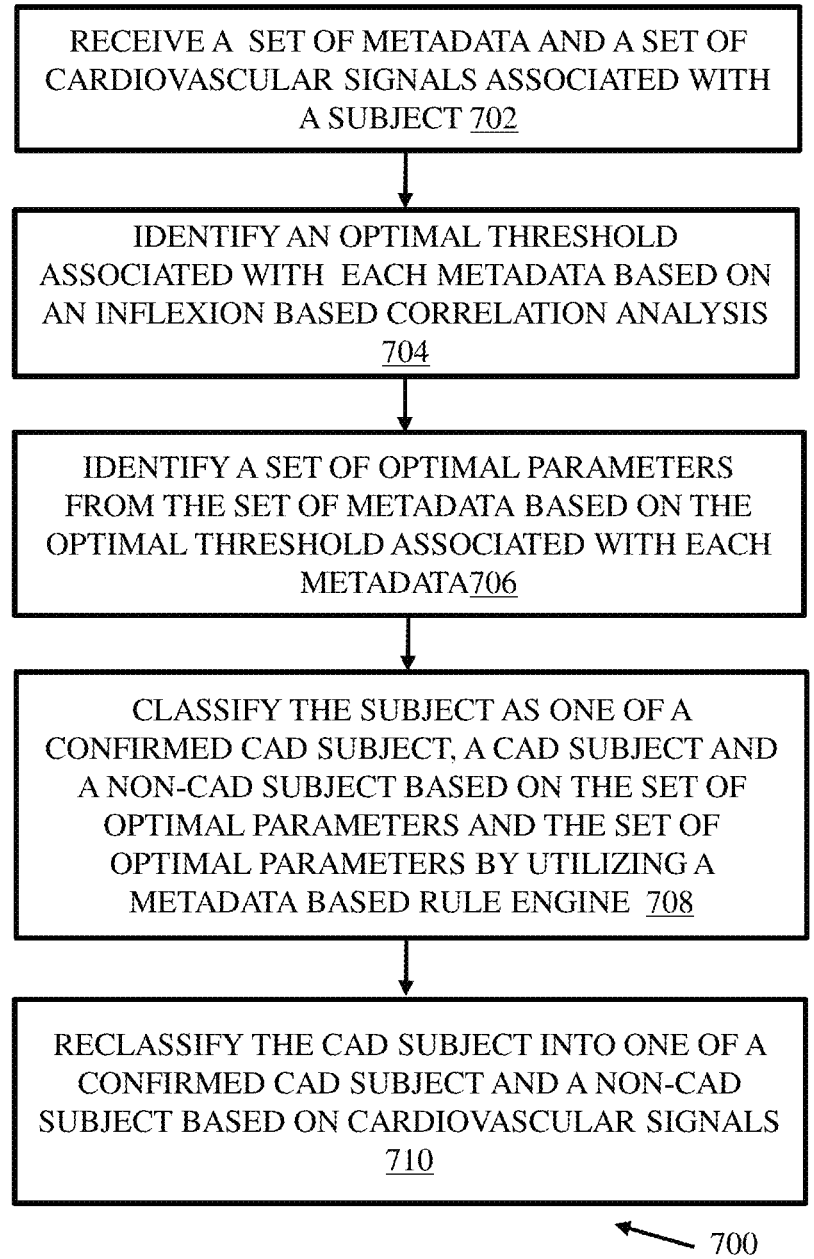
FIG. 7 illustrates a flow diagram for classification of the CAD based on metadata and cardiovascular signals, according to some embodiments of the present disclosure.

FIG. 7 illustrates a flow diagram of a method 700 for the classification of the CAD based on metadata and cardiovascular signals, according to some embodiments of the present disclosure. The method 700 may be described in the general context of computer executable instructions. Generally, computer executable instructions can include routines, programs, objects, components, data structures, procedures, modules, functions, etc., that perform particular functions or implement particular abstract data types. The method 700 may also be practiced in a distributed computing environment where functions are performed by remote processing devices that are linked through a communication network. The order in which the method 700 is described is not intended to be construed as a limitation, and any number of the described method blocks can be combined in any order to implement the method 700, or an alternative method. Furthermore, the method 500 can be implemented in any suitable hardware, software, firmware, or combination thereof.

At 702, the system 200 receives, by the one or more hardware processors, a set of metadata associated with the subject and the set of cardiovascular signal associated with the subject, wherein each metadata from the set of metadata is associated with a set of values. At 704, the system 200 selects, by the one or more hardware processors, the set of optimal parameters from the set of metadata based on a difference in frequency of occurrence of CAD among the disease population and the non-disease population, wherein the difference in frequency of occurrence of CAD among the disease population and the non-disease population is greater than a predefined threshold. At 706, the system 200 computes, by the one or more hardware processors, the optimal threshold for each optimal parameter from the set of optimal parameters based on the inflexion point based correlation analysis. At 708, the system 200 classifies, by the one or more hardware processors, the subject by utilizing the metadata based rule engine into a category among a plurality of categories, wherein the plurality of categories comprising the confirmed CAD subject, the CAD subject and the non-CAD subject, wherein the metadata based rule engine is constructed by utilizing the set of optimal parameters and the optimal threshold associated with each optimal parameter. At 710, the system 200 reclassifies, by the one or more hardware processors, the CAD subject into one of the confirmed CAD subject and the non-CAD subject based on a combination of the PPG signal classifier and the PCG signal classifier in parallel.

Figure 8:
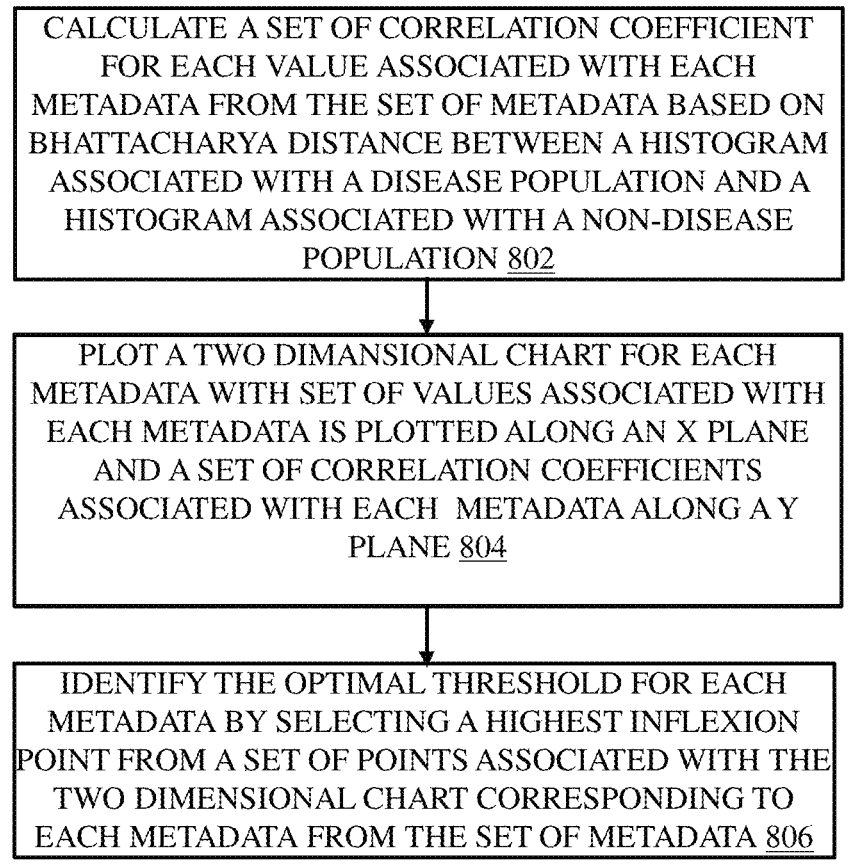
FIG. 8 illustrates a flow diagram for identifying an optimal threshold for each optimal parameter from a set of optimal parameters based on an inflexion point based correlation analysis, according to some embodiments of the present disclosure.

FIG. 8 illustrates a flow diagram for identifying an optimal threshold for each metadata from a set of metadata based on the inflexion point based correlation analysis, according to some embodiments of the present disclosure. At step 802, the set of correlation coefficient for each value associated with each optimal parameter from the set of optimal parameters based on Bhattacharya distance between a histogram associated with the disease population and a histogram associated with the non-disease population is calculated. At step 804, the two dimensional chart for each optimal parameter from the set of optimal parameters, wherein the set of values associated with each optimal parameter is plotted along the X plane and the set of correlation coefficients associated with each optimal parameter is plotted along the Y plane is plotted. At step 806, the optimal threshold for each optimal parameter is identified by selecting a highest inflexion point from the set of points associated with the two dimensional chart corresponding to each optimal parameter from the set of optimal parameters.

Figure 9:
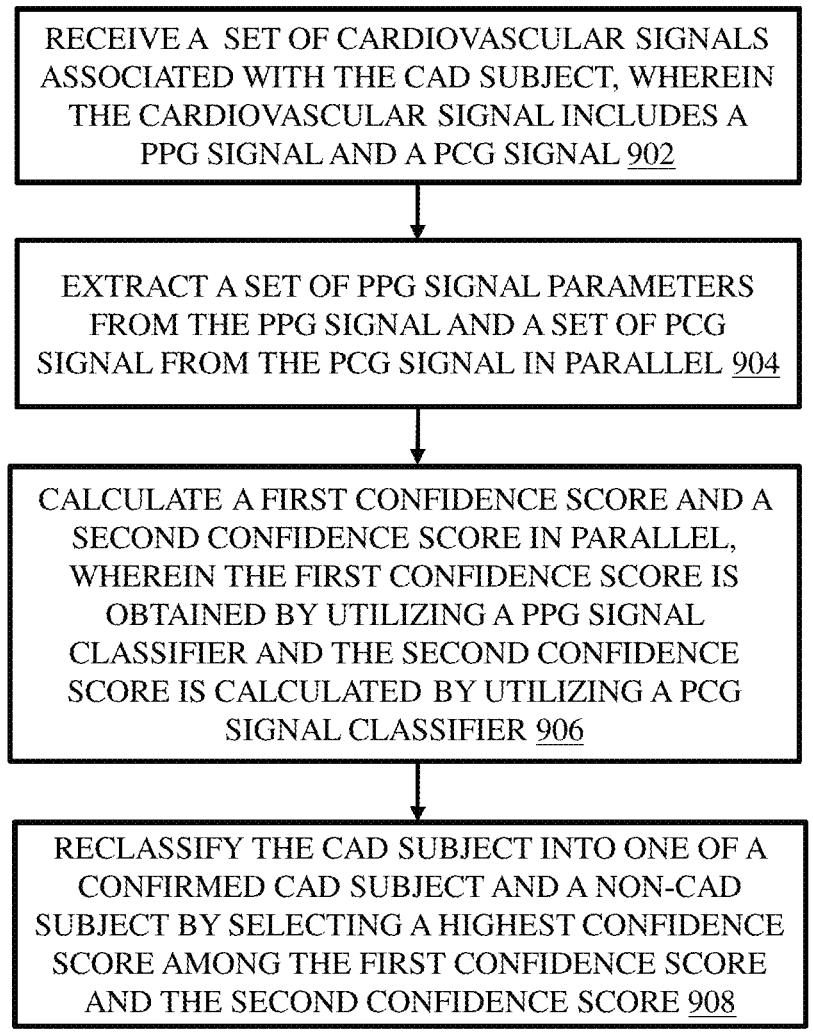
FIG. 9 illustrates a flow diagram for reclassifying a CAD subject based on a combination of the PPG signal classifier and the PCG signal classifier in parallel, according to some embodiments of the present disclosure.

FIG. 9 illustrates a flow diagram for reclassifying the CAD subject based on the combination of the PPG signal classifier and the PCG signal classifier in parallel, according to some embodiments of the present disclosure. At step 902, the set of cardiovascular signal associated with the CAD subject are received, wherein the set of cardiovascular signal comprises the PPG signal and the PCG signal. At step 904, the set of PPG signal parameters from the PPG signal and the set of PCG signal parameters from the PCG signal are extracted in parallel. Here, the set of PPG signal parameters includes the cycle duration, the systolic upstroke time, the diastolic time, the trough to notch time, the notch to trough time, the peak to notch time and the pulse width. Here, the set of PCG signal parameters includes the spectral power ratio, the spectral centroid, the spectral roll-off, the spectral flux, the kurtosis of time windows, the natural entropy, and the Tsallis entropy. At step 906, the first confidence score and the second confidence score are calculated in parallel, wherein the first confidence score is obtained by utilizing the PPG signal classifier and the second confidence score is obtained by utilizing the PCG signal classifier. Here, the PPG signal classifier is trained by utilizing a PPG signal training data, wherein, the PPG signal training data includes the set of PPG signal parameters associated with the disease population and the set of PPG signal parameters associated with the non-disease population. Here, the PCG signal classifier is trained by utilizing a PCG signal training data, wherein, the PCG signal training data includes the set of PCG signal parameters associated with the disease population and the set of PCG signal parameters associated with the non-disease population. At step 908, the CAD subject is reclassified into one of the confirmed CAD subject and the non-CAD subject by selecting a highest confidence score among the first confidence score and the second confidence score.

Figure 10:
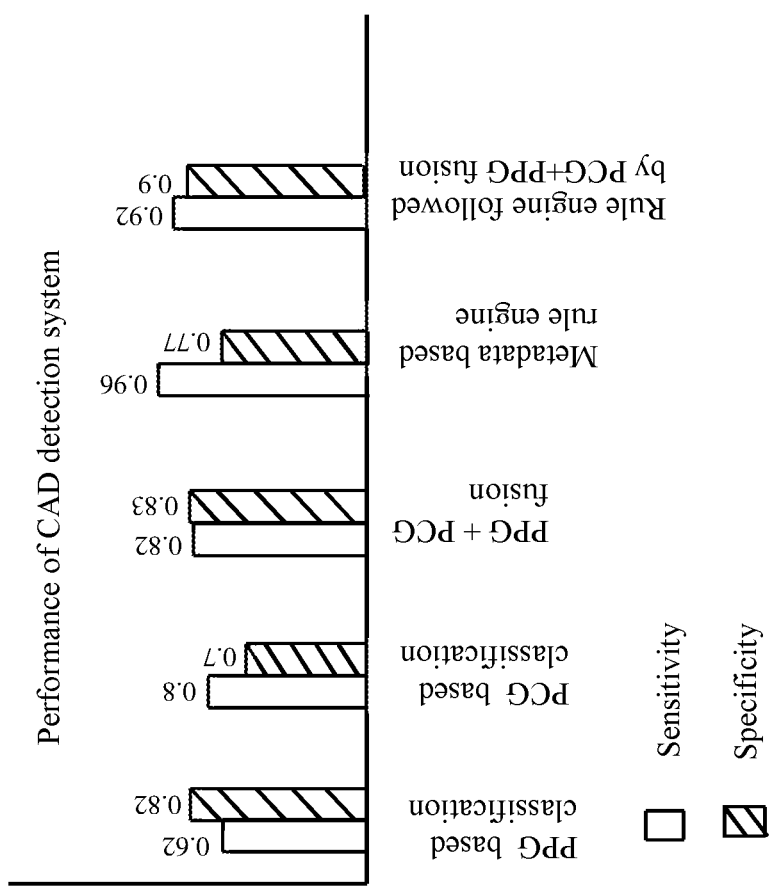
FIG. 10 illustrates a comparative study of individual PCG and PPG classifiers, the metadata based rule engine, a fusion classifier and a two-stage classifier in terms of mean sensitivity and specificity, according to some embodiments of the present disclosure.

In an embodiment, the system 200 is experimented with a dataset comprising a total of 99 subjects. The data set is collected from an urban hospital in India in a balanced ratio of the CAD and the non-CAD subjects, covering diverse patient demography and medical history. Here, a 5-fold cross validation approach is applied on the entire dataset. The subjects classified as the CAD subjects by the metadata based rule engine are sent to the second stage of classification for decision making. The metadata information are typically obtained based on questionnaires to the users. Average values of sensitivity and specificity of classifying the CAD subjects across all the 5 folds are reported as evaluation metrics in the present disclosure. A very high sensitivity is a major requirement for any medical screening system. On the other hand, specificity should also be sufficiently high to reduce the false positive rate in disease detection, which is important for usability purpose. Hence, there is a necessity to achieve high values in both sensitivity and specificity simultaneously, rather than focusing on overall classification accuracy. FIG. 10 illustrates a comparative study of individual PCG and PPG classifiers, metadata based rule engine, fusion classifier and the two-stage classifier in terms of mean sensitivity and specificity, according to some embodiments of the present disclosure. The results indicates that the classifiers designed using a single cardiovascular signal is not sufficient for very accurate disease detection. A promising accuracy with balanced sensitivity and specificity can be achieved by applying the second stage of classification on the entire dataset based on fusion of PPG and PCG classifiers. Here both sensitivity and specificity values reach close to 0.8. However, for many of the borderline CAD subjects having 30% or lesser heart blockage, discriminative markers are not always present in short recordings of cardiovascular signals. This restricts the overall sensitivity and specificity of the system. The metadata based rule engine, yields a very high sensitivity of 0.96 in detecting the CAD subjects. However specificity drops to 0.77 as the rule engine is biased towards the CAD. The proposed two-stage classification technique tries to rectify the misclassification error of the metadata based rule engine by utilizing the cardiovascular signal analysis at second stage for improving the overall specificity of the system to 0.9, minimally affecting the sensitivity (0.92).

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

Various embodiments disclosed methods and system for classification of CAD based on metadata and cardiovascular signals are able to provide an end-to-end solution for accurate classification of the CAD. The combination of the metadata based rule engine utilized in the first stage of classification and the cardiovascular signal based reclassification in the second stage increased the accuracy of the system 200. Further, the system 200 classifies the subjects based on the set of demographic data, the set of clinical information and the set of cardiovascular signals. Moreover, the optimal threshold associated with each optimal parameter is calculated based on the inflexion based correlation analysis and hence the number of false positives and the number of false negatives can be reduced.

It is, however to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software modules located therein. Thus, the means can include both hardware means and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various modules described herein may be implemented in other modules or combinations of other modules. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope and spirit of disclosed embodiments being indicated by the following claims.

What is claimed is:

1. A system for classification of Coronary Artery Disease (CAD) based on metadata and cardiovascular signals, the system comprising:
 one or more memories comprising programmed instructions and a repository for storing a set of metadata associated with a subject and a set of cardiovascular signals associated with the subject, wherein the set of cardiovascular signals comprises a Photoplethysmogram 'PPG' signal and a Phonocardiogram 'PCG' signal;
one or more hardware processors operatively coupled to the one or more memories, wherein the one or more hardware processors are capable of executing the programmed instructions stored in the one or more memories;
a PPG signal capturing device,
a PCG signal capturing device and
a CAD analysis unit, wherein the CAD analysis unit is configured to:
receive, a set of metadata associated with a subject and a set of cardiovascular signal associated with the subject, wherein each metadata from the set of metadata is associated with a value;
select, a set of optimal parameters from the set of metadata based on a difference in frequency of occurrence of CAD among a disease population and a non-disease population, wherein the disease population refers to the population as confirmed CAD subjects and the non-disease population refers to the population as non-CAD subjects;
compute, an optimal threshold for each optimal parameter from the set of optimal parameters by utilizing an inflexion point based correlation analysis, wherein the inflexion point based correlation analysis is derived from the set of metadata based on a difference in frequency of occurrence of CAD among a disease population and a non-disease population;
classify, the subject by utilizing a metadata based rule engine into a category among a plurality of categories, wherein the plurality of categories comprising a confirmed CAD subject, a CAD subject and a non-CAD subject, wherein the metadata based rule engine is constructed by utilizing the set of optimal parameters and the optimal threshold associated with each optimal parameter; and
reclassify, the CAD subject into one of the confirmed CAD subject and the non-CAD subject based on a combination of a Photoplethysmogram 'PPG' signal classifier and a Phonocardiogram 'PCG' signal classifier in parallel, wherein the CAD analysis unit is configured to reclassify the CAD subject into one of the confirmed CAD subjects and the non-CAD subjects by utilizing the PPG signal classifier and the PCG signal classifier in parallel by:
receiving the set of cardiovascular signals associated with the CAD subject, wherein the set of cardiovascular signals comprises the PPG signal and the PCG signal;
extracting a set of PPG signal parameters from the PPG signal and a set of Phonocardiogram 'PCG' signal parameters from the PCG signal in parallel;
calculate a first confidence score and a second confidence score in parallel, wherein the first confidence score is obtained by utilizing the PPG signal classifier and the second confidence score is obtained by utilizing the PCG signal classifier, wherein the set of PPG signal parameters are classified by utilizing the PPG signal classifier to obtain the first confidence score, and the set of PCG signal parameters are classified by utilizing the PCG signal classifier to obtain the second confidence score; and
reclassifying the CAD subject into one of the confirmed CAD subject and the non-CAD subject by selecting a highest confidence score among the first confidence score and the second confidence score.

2. The system as claimed in claim 1, wherein the CAD analysis unit is configured to identify the optimal threshold for each optimal parameter from the set of optimal parameters based on the inflexion point based correlation analysis by:
calculating a set of correlation coefficient for each value associated with each optimal parameter from the set of optimal parameters based on Bhattacharya distance between a histogram associated with the disease population and a histogram associated with the non-disease population;
plotting a two dimensional chart for each optimal parameter from the set of optimal parameters, wherein, the set of values associated with each optimal parameter is plotted along an X plane and the set of correlation coefficients associated with each optimal parameter is plotted along a Y plane; and
identifying the optimal threshold for each optimal parameter by selecting a highest inflexion point from a set of points associated with the two dimensional chart corresponding to each optimal parameter from the set of optimal parameters.

3. The system as claimed in claim 1, wherein the set of metadata comprising a set of demographic data and a set of clinical information.

4. The system as claimed in claim 1, wherein the set of PCG signal parameters comprises a spectral power ratio, a spectral centroid, a spectral roll-off, a spectral flux, a kurtosis of time windows, a natural entropy, and a Tsallis entropy.

5. The system as claimed in claim 1, wherein the set of PPG signal parameters comprises a cycle duration, a systolic upstroke time, a diastolic time, a trough to notch time, a notch to trough time, a peak to notch time and a pulse width.

6. The system as claimed in claim 1, wherein the PPG signal classifier is trained by utilizing a PPG signal training data, wherein, the PPG signal training data includes the set of PPG signal parameters associated with the disease population and the set of PPG signal parameters associated with the non-disease population.

7. The system as claimed in claim 1, wherein the PCG signal classifier is trained by utilizing a PCG signal training data, wherein, the PCG signal training data includes the set of PCG signal parameters associated with the disease population and the set of PCG signal parameters associated with the non-disease population.

* * * * *